United States Patent [19]

Kodama et al.

[11] Patent Number: 4,683,894
[45] Date of Patent: Aug. 4, 1987

[54] DISPOSABLE PHYSIOLOGICAL PRESSURE SENSING SYSTEM

[75] Inventors: Roy K. Kodama, Thousand Oaks, Calif.; Donald J. Koneval, Arlington Heights, Ill.

[73] Assignee: Gould, Inc., Rolling Meadows, Ill.

[21] Appl. No.: 629,298

[22] Filed: Jul. 9, 1984

[51] Int. Cl.$^4$ .............................................. A61B 5/02
[52] U.S. Cl. ................................... 128/675; 128/748; 73/708
[58] Field of Search ................................ 128/672–673, 128/675, 748; 73/706, 708, 715–720; 338/2–3

[56] References Cited

U.S. PATENT DOCUMENTS

| | | | |
|---|---|---|---|
| 3,553,625 | 1/1971 | Stedman | 128/675 X |
| 3,675,891 | 7/1972 | Reynolds et al. | |
| 3,818,765 | 6/1974 | Eriksen | 128/675 X |
| 4,192,303 | 3/1980 | Young et al. | |
| 4,245,636 | 1/1981 | Sparks et al. | |
| 4,274,423 | 6/1981 | Mizuno et al. | 128/675 |
| 4,291,702 | 9/1981 | Cole et al. | 128/675 |
| 4,572,204 | 2/1986 | Stephens | 128/748 X |

FOREIGN PATENT DOCUMENTS

84/00291  2/1984  PCT Int'l Appl. ............... 128/672

*Primary Examiner*—Kyle L. Howell
*Assistant Examiner*—Angela D. Sykes
*Attorney, Agent, or Firm*—Lyon & Lyon

[57] ABSTRACT

A physiological pressure sensing and monitoring system including a sterile throwaway pressure transducing device. The device includes a pressure transducer mounted together with a flow control valve in a housing. The device includes a first connector for connecting the device to a source of sterile solution, a second connector for electrically connecting the pressure transducer to a monitoring device, and a third connector for selectively connecting the device to a catheter inserted into a patient's circulatory system. The device, including the connectors, is made to be low cost so as to permit the entire device to be installed and discarded as a unit so as to constitute a throwaway pressure sensing and flow regulator. The pressure transducer includes a novel mounting of the strain gage beam to the isolator which has been found to effectively avoid cracking and breaking of the beam from the stress forces applied thereto in the operation of the device. In the illustrated embodiment, the lower surface of the beam is secured to the upper surface of the isolator, and the upper surface of the beam is engaged by a link connected to a displaceable diaphragm. The isolator is connected by a pair of supports to a frame such that thermally induced stresses in the frame do not affect the zero-point of the strain gage.

9 Claims, 7 Drawing Figures

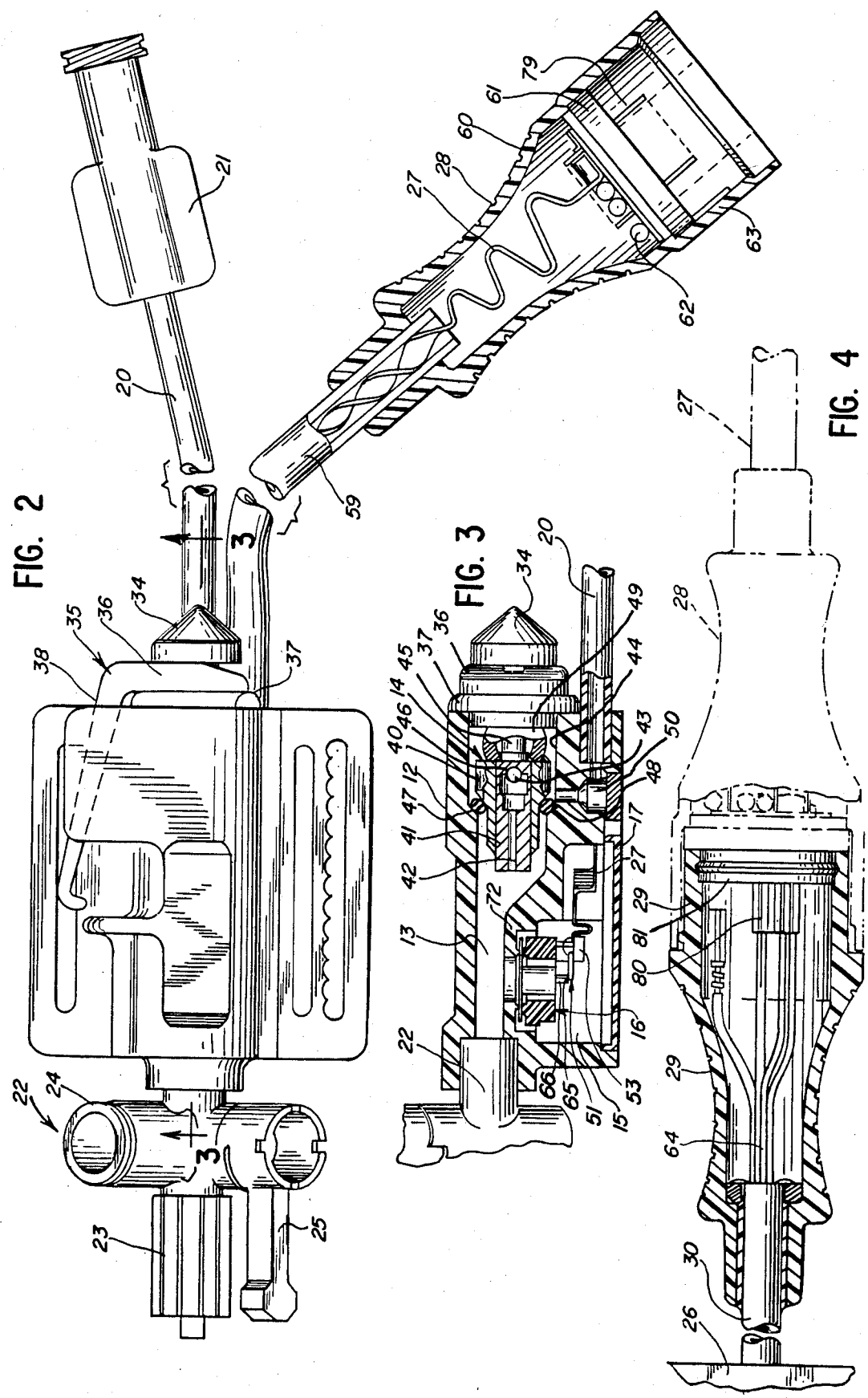

DISPOSABLE PHYSIOLOGICAL PRESSURE SENSING SYSTEM

BACKGROUND OF THE INVENTION

1. Field of the Invention

This invention relates to physiological pressure sensing systems, and in particular to such a system utilizing a disposable pressure transducer having a cantilevered stain gage sensor and embodying a design which minimizes effects of thermally induced stresses.

2. Description of the Background Art

An improved flow control apparatus for use in fluid flow systems, such as for monitoring blood pressure in humans and other animals, is disclosed in U.S. Pat. No. 4,291,702 of James E. Cole et al., which patent is owned by the assignee hereof. As disclosed therein, the flow control apparatus is adapted for use with catheters, such as used in invasive blood pressure monitoring by insertion into a patient's artery or vein. In normal use in such systems, a source of a sterile isotonic solution is connected to the catheter and the solution is caused to flow through the catheter into the patient at a low flow rate sufficient to maintain the catheter open and unclogged as by blood constituents and the like at the inserted end of the catheter.

As further pointed out in the Cole et al. patent, the catheter system is firstly flushed of air before insertion of the catheter into the patient. To permit the system to be rapidly filled with the sterile solution which is used to flush the system of air, the flow control apparatus of said patent further is arranged to selectively permit a high flow rate of the solution from the source to the catheter.

In one embodiment of the apparatus disclosed in the Cole et al. patent, a flexible diaphragm is extended across an opening to the pressure chamber of the housing of the apparatus. Means are provided for connecting a fluid actuated transducer to the housing so that deflections of the diaphragm cause corresponding deflections of the transducer.

A problem has arisen in the use of such systems relative to the high expense and unreliability of the pressure transducers employed. Such transducers have been quite expensive in order to provide the necessary accuracy. As the transducers must be cleaned and sterilized from time to time, the useful life thereof has been relatively short because repeated cleaning and sterilization renders them inoperative. Such inoperativeness presents a particularly vexatious problem in that it normally is discovered at the critical time of setting up the system with the patient since testing of the apparatus is impractical immediately after cleaning and sterilization.

Further, the use of reusable pressure transducers may cause cross-contamination and spreading of infection where complete cleaning and sterilization are not effected.

In one known form of an improved physiological pressure sensing system disclosed in copending application Ser. No. 398,399 of Schaberg et al., filed July 14, 1982, now U.S. Pat. No. 4,545,389 and owned by the assignee hereof, the high cost and unreliability problems of the prior art systems are eliminated by the provision of an improved throwaway device including a fast-slow flow control means and a pressure transducer means in a single housing. This device comprises a low-cost, high-accuracy transducer effectively permitting throwaway use of the device so that the device may be used with a single patient only, thereby completely avoiding cross-contamination and infection.

The device further includes means for connecting the source of sterile isotonic solution thereto and means for connecting the patient catheter thereto, and eletrical connection means for connecting electrical output means of the pressure transducer to an external monitor and the like, the connecting means comprising portions of the throwaway device.

The means for controlling solution flow from the source, such as an elevated bag or container, further includes flow restrictor means which maintains the pressure chamber of the device substantially at the patient's blood pressure, notwithstanding the continual delivery of solution at a low rate therethrough to the catheter for maintaining the catheter unclogged, as discussed above.

The pressure transducer sensing means is electrically isolated from the fluid in the pressure chamber so as to effectively prevent damage to the pressure transducer as by application of high voltages and transient electrical pulses of 400 to 500 joules such as may be applied to the patient in effecting certain treatments. Alternatively, the electrical isolation of the transducer from the pressure chamber avoids transfer of electrical current from the external monitoring system and, thus, effectively isolates the patient from a short circuit in the external system.

Pressure relief means are provided for preventing high pressure conditions which may appear in the pressure chamber from damaging the pressure transducer.

The arrangement of the device as a throwaway device permits it to be packaged and stored in sterile condition until desired for use. At that time, the sterile sealed package is opened and the system filled with sterile isotonic solution to facilitate invasive connection to the patient. The device provides a complete interconnection system between the source of sterile solution, the electrical monitoring apparatus, and the patient, and, thus, completely eliminates the possibility of cross-contamination, as well as assuring that a reliable new system is available for immediate use.

The housing and other components of the system are formed from low-cost molded synthetic resins, such as polycarbonate, having high strength, chemical and electrical resistance, and dimensional stability.

The pressure transducer utilizes a strain gage comprising a diffused pattern on a cantilevered single crystal silicon beam providing the major spring restraint in the pressure transducer. A flexible cable of electrical conductors is connected to the strain gage by suitable fine wires.

The pressure transducer includes a force collector including a diaphragm, a frame, and a link for connecting the diaphragm to the deflectible beam. The beam is provided with strain gage means. Illustratively, the beam is formed of silicon, with a resistive strain gage grid fused thereinto. The beam is mounted to the frame by an isolator for reducing the effect on the strain gage means of stresses which may be induced in the frame. In particular, one end of the upper surface of the beam is affixed to the isolator and the other end of such surface is connected to the link with the lower surface of the beam being free.

Low-cost manufacture is effected by forming the three elements of the force collector as a one-piece unit, and by forming the beam as a wafer element having a thickness of approximately 0.01 inch.

The discussed throwaway pressure monitoring device is extremely simple and economical of construction while yet providing highly desirable features as discussed above.

SUMMARY OF THE INVENTION

The above-described pressure sensor is an excellent device, providing low-cost, accurate sensing of pressure conditions in physiological applications. It has been found, however, that repeated application of substantial flexing forces on the cantilevered deflectible strain gage beam has shortened the useful life thereof as by causing cracking or fracturing of the beam.

Also, a large surface area of the isolator is affixed directly to the frame and if the isolator and frame are made of different materials, thermally induced stresses in the frame are transferred to the isolator causing the isolator and beam to deform, thus shifting the zero-point of the strain gage.

The present invention provides novel, simple, low-cost solutions to these problems.

In the illustrated embodiment, one end of the lower surface of the beam is affixed to the isolator and the other end of the upper surface of the beam is connected to the link of the force collector. It has been unexpectedly found that such a support of the beam substantially avoids the cracking and fracturing problem of the prior devices as discussed above.

Additionally, in the illustrated embodiment, the isolator is carried in spaced relationship to the frame by a pair of transversely spaced mounting supports, thereby minimizing the transfer of thermally induced stresses from the frame to the isolator.

BRIEF DESCRIPTION OF THE DRAWING

Other features and advantages of the invention will be apparent from the following description taken in connection with the accompanying drawing wherein:

FIG. 2 is a fragmentary plan view of the throwaway device;

FIG. 3 is a fragmentary vertical section taken substantially along the line 3—3 of FIG. 2;

FIG. 4 is a fragmentary diametric section illustrating the connection of a reusable connector associated with the monitoring apparatus, with the disposable electrical connector portion of the throwaway device;

DESCRIPTION OF THE PREFERRED EMBODIMENT

Figure 1:
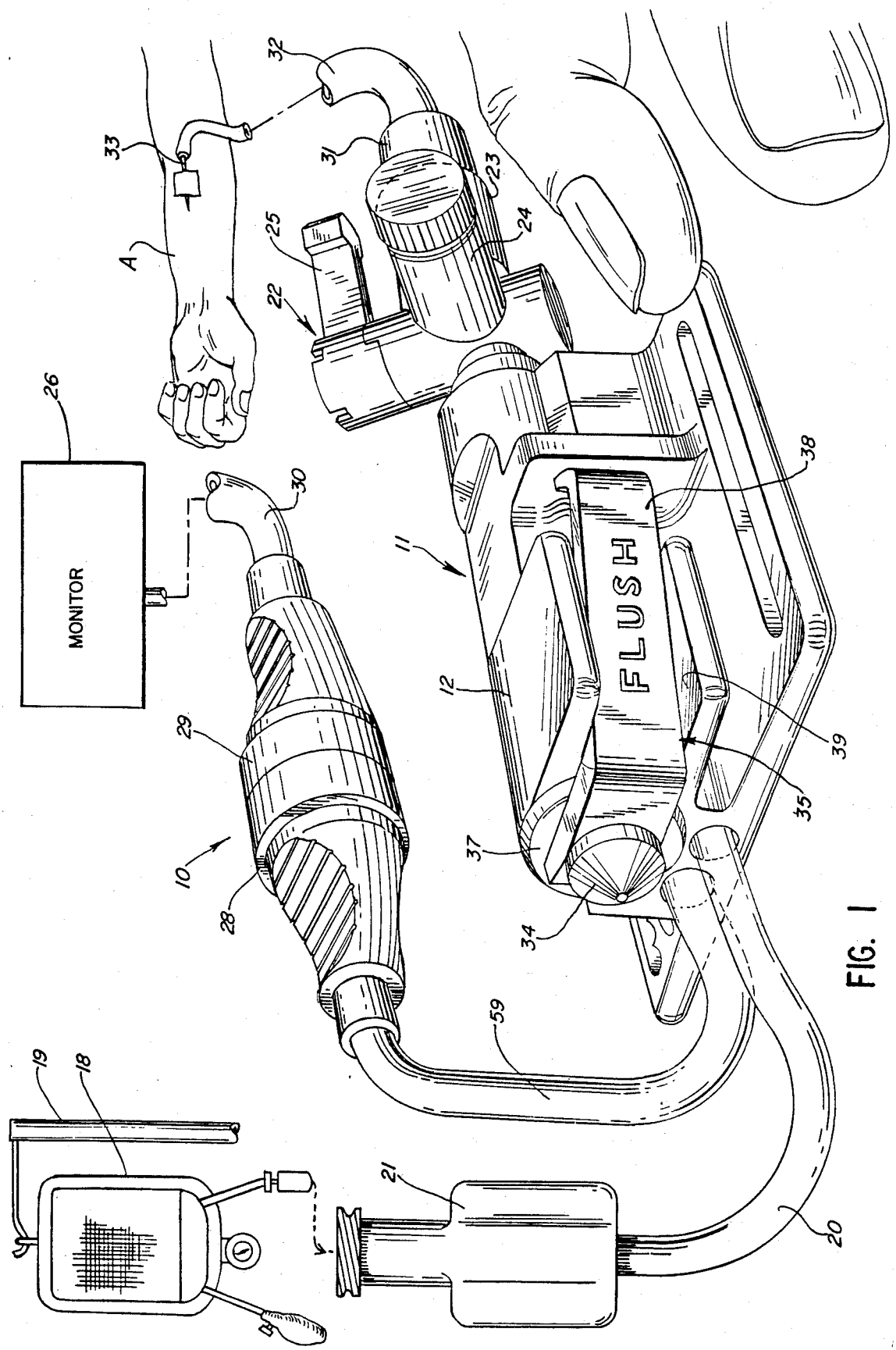
FIG. 1 is a broken perspective view of a disposable physiological pressure sensing system embodying the invention for association with a source of sterile isotonic solution, monitoring apparatus, and a catheter adapted to be inserted into a patient's circulatory system.

In the exemplary embodiment of the invention as shown in the drawing, a disposable, physiological pressure sensing system gererally designated 10 is shown to comprise a device 11 having a housing 12, which, as seen in FIG. 3, defines a pressure chamber 13, at one end of which is received a flow control valve 14.

As further illustrated in FIG. 3, housing 12 further defines a transducer chamber 15 in which is mounted a pressure transducer 16. Chamber 15 is selectively closed by a closure element 17.

Sterile isotonic solution, such as saline solution, is provided to chamber 13 from an external pressurized source, such as bag device 18 illustrated in FIG. 1, carried on a suitable standard 19 suitably adjusted to provide a controlled pressure delivery (conventionally at approximately 300 millimeters of mercury) of the solution therefrom through a conduit 20 connected to the bag device 18 by a conventional connector 21. From pressure chamber 13, the sterile solution is delivered through a connector generally designated 22, which, in the illustrated embodiment, comprises a stopcock, selectively connecting the pressure chamber to a luer connector 23, or a bypass connector 24, as a result of suitable manipulation of a handle 25. Flow of saline solution from connector 23 is effected through a connector 31 at the distal end of a conduit 32 terminating in a catheter 33 providing an invasive connection to the patient when inserted into a blood vessel of the patient.

Pressure transducer 16 provides an electrical output signal corresponding to the pressure of fluid in pressure chamber 13, which is transmitted to an external monitor 26 of conventional construction through a cable 59 terminating in a connector 28. Connector 28 is adapted to have readily separable connection to a connector 29 connected to monitor 26 through a cable 30.

Thus, the boundaries of device 11 are defined by connectors 21, 28 and 23 so that the device may be provided as an integral assembly readily connected into the system wherein the external components comprise saline solution source bag device 18, monitoring apparatus 26, and connection 31 to the conduit connected to the patient.

As further illustrated in FIG. 1, flow control valve 14 is provided with an angle operator 35 which, when depressed, moves the valve to an open position, permitting a high rate of flow of the saline solution from bag device 18 into pressure chamber 13. As best seen in FIG. 2, operator 35 includes an apertured end portion 36 extending between a boss 34 and a cap 37 on housing 12 sealing the end of pressure chamber inlet portion 44. A finger-actuated portion 38 extends angularly to portion 36 and is received in a space 39 so that when the portion 38 is urged inwardly toward housing 12, portion 36 is rocked outwardly to urge boss 34 outwardly and thereby pull valve 14 connected thereto to an open position.

More specifically, valve 14 is generally similar to and functions in a manner generally similar to the fast-flush valve disclosed in the above discussed U.S. Pat. No. 4,291,702, which patent is incorporated by reference herein. Briefly, however, valve 14 is defined by a valve body 40 having a through bore receiving a cylindrical insert 41 provided with a capillary bore 42 illustratively having a diameter of approximately 0.002 inch. At its outer end, the insert is provided with radially opening passages 43 which are aligned with similar passages in valve body 40, thereby providing passages for conducting saline solution from inlet portion 44 into insert 41 from which solution is metered outwardly through capillary bore 42 into pressure chamber 13.

As further illustrated in FIG. 3, boss 34 is connected to a stem 45 bonded to the outer end 46 of insert 41, so that when boss 34 is urged outwardly by operator 35, as discussed above, body 40 and insert 41 are pulled outwardly to disengage the body from an annular O-ring seal 47 and thereby provide a flow path from inlet portion 44 around the seal to pressure chamber 13. The valve is biased to the closed position wherein body 40 seats against O-ring 47 which, in turn, is urged against a frustoconical shoulder 48 between inlet portion 44 and pressure chamber 13 by a resilient tube 49 extending axially between valve body 40 and cap 37. As shown in FIG. 3, the length of tube 49 is slightly greater than the space between body 40 and cap 37 so that the tube is under compression, thereby providing the desired biasing of the valve to the closed disposition illustrated in FIG. 3 and sealing the cap to valve body 40 about stem 45.

As further-shown in FIG. 3, supply conduit 20 is connected to inlet portion 44 through a passage 50 opening to portion 44 adjacent O-ring 47.

The resiliency of tube 49 is preselected to permit outward movement of the valve body as a result of an increase in pressure in pressure chamber 13 to an undesirably high pressure so as to relieve the pressure by directing the isotonic saline solution back to bag source 18 and thereby prevent damage to the transducer from such high-pressure conditions or surges.

Figure 5:
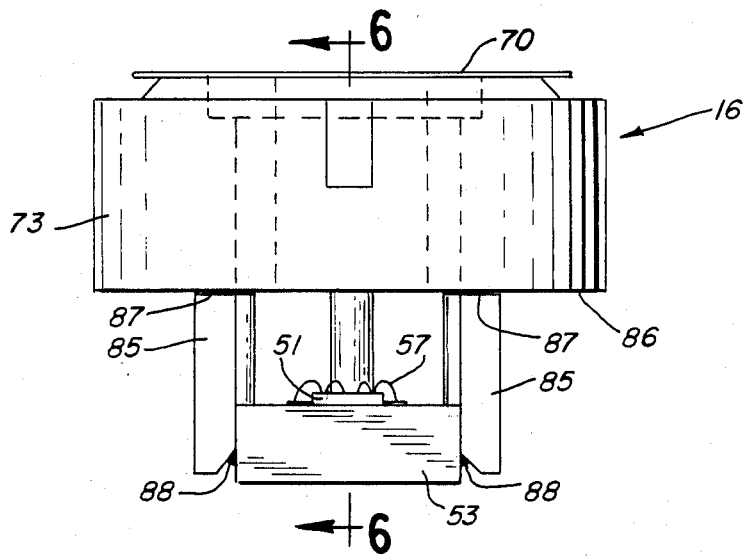
FIG. 5 is a front elevation of the pressure transducer illustrating the mounting of the beam to the isolator and the connection of the isolator to the frame.
Figure 6:
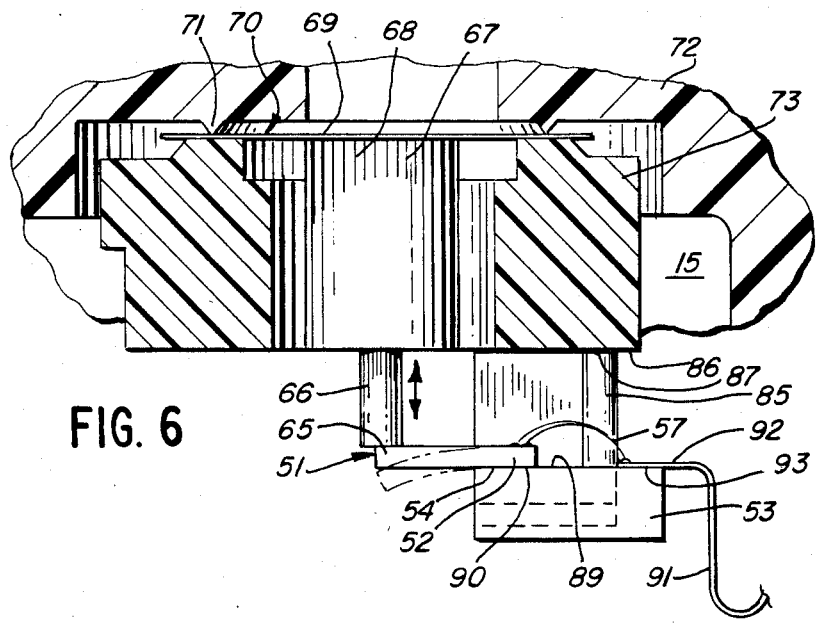
FIG. 6 is a fragmentary enlarged vertical section taken substantially along the line 6—6 of FIG. 5.
Figure 7:
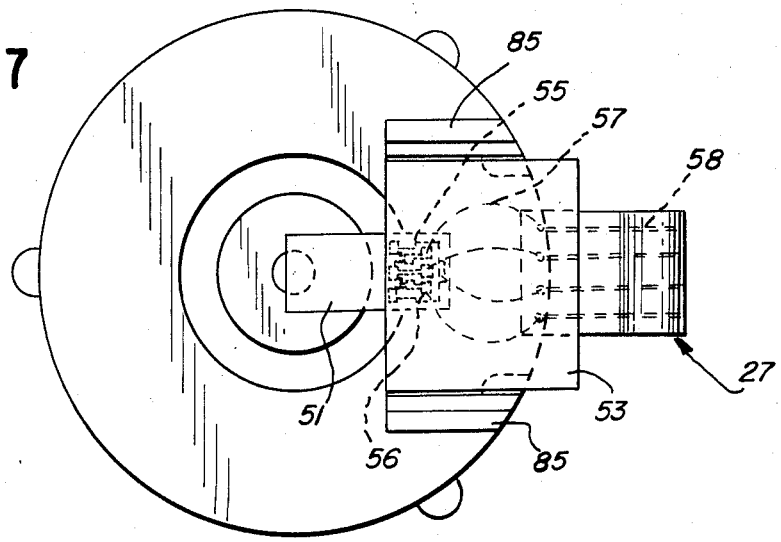
FIG. 7 is a fragmentary bottom plan view of the transducer.

As indicated briefly above, the invention comprehends the provision in housing 12 in combination with flow control valve 14 of pressure transducer 16, permitting the pressure transducer to be included with the other components of the device for throwaway use of the entire system by virtue of the low-cost construction thereof. In the illustrated embodiment, as shown in FIGS. 5-7, the pressure transducer includes a deflectible beam 51 having one end 52 secured to a strain isolator 53 as by electrostatic bonding 54, or suitable adhesive means. Beam end 52 is provided with a wheatstone bridge strain gage 55. In the illustrated embodiment, the strain gage resistance grid is fused into the beam which, illustratively, may be formed of a suitable deflectible material, such as silicon, etc. The beam preferably has a wafer thickness of approximately .01 inch for facilitated manufacture and defines the major restraint component of the pressure transducer. Preferably, isolator 53 is formed of glass.

As further indicated in FIG. 7, the strain gage bridge includes a plurality of pads 56 to which fine gold alloy wires 57 are electrically connected at one end. As shown in FIG. 7, at the opposite end wires 57 are electrically connected to flat conductors 58 of a wire bundle 27 of cable 59.

As illustrated in FIG. 2, the distal end of wire bundle 27 is received in a connector head 60 and connected to a connector plate 61 thereof through calibrating resistors 62. The calibrating resistors are calibrated by laser trimming in a conventional manner so as to calibrate the pressure transducer accurately for clinical use. As further shown in FIG. 2, the head 60 defines a distal socket portion 63 for receiving the male connector 29 (see FIG. 4). The male connector houses the end of a wire bundle 64 of cable 30 for providing connection from connector plate 61 to the monitor apparatus 26, as illustrated in FIG. 4. As indicated above, the male connector 29 and cable 30 are reusable components of the overall system, being separable from connector 28 for disposal of the device 11 as a whole.

In the illustrated embodiment, connector plate 61 is provided with a plurality of connector pins 79 aligned with and adapted to be received in suitable female connectors 80 in a connector plate 81 in connector head 29.

In the preferred embodiment of pressure transducer 16 as illustrated in FIGS. 5-7, the distal end 65 of beam 51 is connected to a projecting pin portion 66 of a small diameter link 67 having its opposite end 68 connected to the midportion 69 of a diaphragm 70. Diaphragm 70 is bonded to an annular rib 71 on housing wall 72 separating pressure chamber 13 from transducer space 15.

A frame generally designated 73 extends coaxially oppositely of rib 71 from the opposite face of the diaphragm. Strain isolator 53 is mounted to frame 73 by a pair of transversely spaced-apart mounting supports 85, preferably formed of molded polycarbonate, and having their upper ends bonded to the lower surface 86 of the frame by suitable means, such as epoxy cement 87. Strain isolator 53, as shown in FIG. 5, may be secured to the lower ends of supports 85 by suitable means, such as epoxy cement 88. Thus, isolator 53 is mounted in downwardly spaced relationship to frame lower surface 86, permitting beam end 52 to be secured to the upper surface 89 of isolator 53.

By the use of mounting supports 85 for spacing the upper surface 89 of isolator 53 downwardly from frame lower surface 86, the isolator is effectively insulated from deformation along surface 89 resulting from thermally induced stresses in frame 73. While thermally induced stresses in the frame and supports may result in some slight vertical movement of the ends of the isolator, such movement has only negligible effect, if any, on the central portion of the isolator where beam 51 is mounted. Thus, thermally induced stresses in frame 73 do not shift the zero-point of strain gage 55.

Diaphragm 70 is formed of a compliant material so as to be highly flexible, and in the illustrated embodiment, comprises a disc of polycarbonate having a thickness of 0.002 inch. Frame 73, in the illustrated embodiment, comprises an annular element formed of molded polycarbonate, and link 67 comprises a cylindrical element formed of molded polycarbonate. The link, diaphragm, and frame may be molded as a one-piece force collector structure. Alternatively, the link, diaphragm, and frame may be separately formed and secured together. Thus, the frame may be secured to the diaphragm by a cyanoacrylate bonding agent, and the diaphragm may be sealed to the link by suitable polycarbonate solvent. The diaphragm, in turn, may be secured to housing rib 71 by a suitable polycarbonate solvent.

As indicated, isolator 53 may be secured to beam end 52 by an epoxy adhesive. As indicated above, the beam comprises a 0.01 inch thick wafer of a suitable relatively stiff material so as to provide a major restraint portion of the force transducer.

It has been unexpectedly found that, by mounting beam 51 to isolator upper surface 89, the problem of cracking or breaking of the beam, as has occurred at times with the previous device, is effectively eliminated. It is believed that this improved performance is achieved by eliminating any notch-type structure at a surface of beam 51 which is placed in tension. In other words, the "notch" formed between the lower surface of beam 51 and upper surface 89 of isolator 53 affects only the lower beam surface which is placed in compression during the operation of transducer 16. As shown in FIG. 6, the wires 57 may be connected to wire bundle 27 by a connecting portion 91, the end 92 of which is secured to upper surface 89 of the isolator by suitable electrically insulating cement 93.

The invention comprehends that the resistance to deflection in the strain gage be provided primarily by beam 51 rather than by diaphragm 70. In the illustrated embodiment, the beam comprises a single crystal deflectible member, such as a silicon wafer member, with strain gage bridge 55 being diffused into the silicon wafer surface. Calibration of the system is readily effected, as discussed above, by trimming external resistors 62.

In use, pressure sensing system 10 is set up, as illustrated in FIG. 1, with device 11 interconnected between the source of sterile solution, the output monitoring device, and the patient. As shown in FIG. 1, connector 21 provides a ready connection to the source of sterile solution, bag device 18. Connector 28 provides means for readily connecting the device to monitor connector 29, and connector 22 provides means for readily connecting the device to catheter 33 through connector 31.

Stopcock connector 22 permits the taking of blood samples by selectively positioning handle 25 so as to discharge blood from the patient through connector 24. The stopcock is arranged so as to close all connections, when desired.

As discussed above, the fast-flush valve is readily manually operable by the simple depression of finger-actuated portion 38 of operator 35. Thus, the initial filling of the system with sterile solution may be effected by the opening of valve 14 by the depression of portion 38. As discussed above, in the closed position of the valve, a small flow passage is maintained through the passages 43 and capillary bore 42 so as to continuously provide a flow of sterile saline solution through the system and catheter and thereby maintain the catheter unclogged by the patient's blood constituents.

The device may be maintained connected to the patient notwithstanding the application of high potentials to the patient, such as defibrillation potentials, as the pressure transducer sensing strain gage is electrically isolated from the fluid in the pressure chamber. As indicated above, the electrical isolation further prevents injury to the patient as from electrical potentials appearing on the sensor beam from electrical failure of the output elements, such as monitor 26.

As the cost of device 11 is relatively low, upon completion of the use thereof with a given patient, the entire device, up to and including connectors 21, 28 and 22, as well as the patient line, may be discarded so as to effectively eliminate any possibility of cross-contamination with other patients. Such low cost is effected in device 11 while yet providing high accuracy and long, trouble-free life as is necessary for clinical use.

The foregoing disclosure of specific embodiments is illustrative of the broad inventive concepts comprehended by the invention.

We claim:

1. In a throwaway physiological pressure system having a housing, improved sensor means comprising:
    displaceable means connected to said housing and responsive to fluid pressure to provide a reciprocative output corresponding to said fluid pressure;
    a strain isolator connected to said housing by a support and having a beam support surface, said support engaging a surface of said isolator other than said beam support surface and positioning said isolator so that said beam support surface is spaced from said housing, whereby said beam support surface is substantially free from thermally induced distortion caused by heat flow from said isolator to said housing and from said housing to said isolator;
    a deflectible beam defining opposite first and second surfaces, a distal end and a mounting end;
    means affixed to said beam and responsive to deflections of said beam for providing corresponding strain signals; and
    means for mounting said mounting end of the beam to said strain isolator with said second surface fixed to said beam support surface and with said distal end cantilevered from said strain isolator, said first surface being engaged by said displaceable means adjacent said distal end, whereby upon deflection of said beam by said displaceable means said first surface is placed in tension and said second surface is placed in compression.

2. The throwaway physiological pressure system of claim 1 wherein said second surface is adhesively bonded to said beam support surface.

3. The throwaway physiological pressure system of claim 1 wherein said means for providing strain signals comprises a strain gage carried on said first surface.

4. The throwaway physiological pressure system of claim 1 wherein said means for providing strain signals comprises a strain gage carried on said first surface at said mounting end.

5. The throwaway physiological pressure system of claim 1 wherein said beam comprises a resiliently deflectible crystal.

6. The throwaway physiological pressure system of claim 5 wherein said beam comprises a silicon crystal beam.

7. The throwaway physiological pressure system of claim 1 wherein said displaceable means includes a compliant diaphragm adapted to confront the fluid, the pressure of which is to be sensed.

8. The throwaway physiological pressure system of claim 1 wherein said displaceable means includes a frame interposed between said housing and said strain isolator.

9. The throwaway physiological pressure system of claim 8 wherein said strain isolator is connected to said frame by a pair of opposed supports, said supports engaging opposite side surfaces of said isolator.

* * * * *